United States Patent
Liu et al.

(10) Patent No.: US 8,889,392 B2
(45) Date of Patent: Nov. 18, 2014

(54) MONOLIGNOL 4-O-METHYLTRANSFERASES AND USES THEREOF

(75) Inventors: Chang-Jun Liu, Rocky Point, NY (US); Mohammad-Wadud Bhuiya, St. Louis, MO (US); Kewei Zhang, Middle Island, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 333 days.

(21) Appl. No.: 13/284,148

(22) Filed: Oct. 28, 2011

(65) Prior Publication Data

US 2012/0117694 A1    May 10, 2012

Related U.S. Application Data

(60) Provisional application No. 61/407,758, filed on Oct. 28, 2010.

(51) Int. Cl.
*C12N 9/10* (2006.01)
*C07H 21/04* (2006.01)
*C12N 15/82* (2006.01)

(52) U.S. Cl.
CPC .......... *C12N 9/1007* (2013.01); *C12N 15/8255* (2013.01); *C12Y 201/01146* (2013.01)
USPC ........ 435/193; 536/23.2; 435/320.1; 800/298

(58) Field of Classification Search
None
See application file for complete search history.

(56) References Cited

FOREIGN PATENT DOCUMENTS

WO    WO 9850570 A2 * 11/1998
WO    WO 03105723    * 12/2003

OTHER PUBLICATIONS

Wang et al, 1999, Archives of Biochem. & Biophysics, 368:172-180.*
Bhuiya, M., et al., "A Cost-Effective Colorimetric Assay for Phenolic O-methyltransferases and Characterization of Caffeate 3-O-Methyltransferases from *Populus trichocarpa*," *Analytical Biochemistry*, vol. 384, pp. 151-158, 2009.
Bhuiya, M., et al., "Engineering Monolignol 4-O-Methyltransferases to Modulate Lignin Biosynthesis," *The Journal of Biological Chemistry*, vol. 285, No. 1, pp. 277-285, 2010 and supplementary material pp. 1-9 [online] [retrieved Oct. 28, 2010 from: jbc.org/content/suppl/2009/10/29/M109.036673.DC1.html>].
Brookhaven National Laboratory News Release, "Making New Enzymes to Engineer Plants for Biofuel Production," No. 1021, pp. 1-2, Dec. 21, 2009, [online] [retrieved May 30, 2012 from: bnl.gov/bnlweb/pubaf/pr/PR_print.asp?prID=1021>.
Brookhaven National Laboratory News Release, "Scientists Unravel More Details of Plant Cell-Wall Construction," No. 1209, pp. 1-3, Dec. 13, 2010, [online] [retrieved May 30, 2012 from: bnl.gov/bnlweb/pubaf/pr/Pr_printasp?prID=1209>].
Chapple, C., et al., "Loosening Lignin's Grip on Biofuel Production," *Nature Biotechnology*, vol. 25, No. 7, pp. 746-748, 2007.
Somerville, C., "Biofuels," *Current Biology*, vol. 17, No. 4, pp. R115-R119, 2007 [online] [retrieved May 7, 2013 from: sciencedirect.com/science/article/pii/S0960982207008111>].
Wang, J., et al., "Characterization of S-Adenosyl-L-Methionine: (Iso)eugenol O-Methyltransferase Involved in Floral Scent Production in *Clarkia breweri*," *Archives of Biochemistry and Biophysics*, vol. 349, No. 1, pp. 153-160, 1998.
Wang, J., et al., "Identification of Specific Residues Involved in Substrate Discrimination in Two Plant O-Methyltransferases," *Archives of Biochemistry and Biophysics*, vol. 368, No. 1, pp. 172-180, 1999.

* cited by examiner

*Primary Examiner* — David H Kruse
*Assistant Examiner* — Jason Deveau Rosen
(74) *Attorney, Agent, or Firm* — Dorene M. Price; Christine L. Brakel

(57) ABSTRACT

Modified (iso)eugenol 4-O-methyltransferase enzymes having novel capacity for methylation of monolignols and reduction of lignin polymerization in plant cell wall are disclosed. Sequences encoding the modified enzymes are disclosed.

11 Claims, 2 Drawing Sheets

MONOLIGNOL 4-O-METHYLTRANSFERASES AND USES THEREOF

PRIORITY

This application claims priority from U.S. Provisional Application 61/407,758 filed Oct. 28, 2010, the entire contents of which are incorporated herein by reference.

GOVERNMENT SUPPORT

This invention was made with Government support under contract number DE-AC02-98CH10886, awarded by the U.S. Department of Energy. The Government has certain rights in the invention.

BACKGROUND

One of the important strategies in securing our country's energy future lies in producing liquid transportation fuel from renewable cell-wall polymer biomass, Lignin is the second most abundant cell-wall biopolymer. While it is important for plant viability it hinders the degradation of the polysaccharide in the cell wall to simple fermentable sugars for ethanol production. Increased understanding of lignin biosynthesis and efficiently managing plant lignification will greatly facilitate the improvement of feedstock for efficient bioenergy/chemical production.

By comparative structure-function analysis, our studies have gained a detailed understanding of the basis for the regioselective O-methylation of lignin monomeric precursors and for other phenylpropanoids. With this information, we have generated a set of novel enzyme catalysts, namely, monolignol 4-O-methyltransferases (MOMTs). Expressing these novel catalysts in plants introduces non-natural lignin monomers that diminish lignin cross-linking and polymerization, and ultimately reduce lignin content in the cell wall. Particularly, we can create a 4-O-methyltransferase to preferentially methylate the G-lignin precursor, p-coniferyl alcohol, expression of which decreases the incorporation of G-lignin unit and thus alters the S/G ratio.

Lignin, the most abundant terrestrial biopolymer after cellulose, imparts structural integrity to the plant cell wall. However, its presence hinders the degradability of feedstock in biofuel production, thus lowering the biomass conversion efficiency. Despite significant progress in genetic and biochemical studies of the biosynthesis of monolignols, the source materials for lignin and lignans, the mechanism of lignification remains controversial. New methodologies or techniques to manipulate the structure of lignin would be useful for improving biofuel production. During industrial processing, lignin must be degraded to extract cellulose fibers to efficiently convert carbohydrates to liquid biofuel (Chapple, C., et al. (2007) *Nat. Biotechnol.* 25, 746-748; Somerville, C. (2006) Biofuel. *Curr. Biol.* 17, R115-R119).

Lignin precursors are exclusively O-methylated at their meta-positions (i.e., 3/5-OH) of the phenyl rings, and are precluded from the substitution at the para-hydroxyl position. In fact, the para-hydroxyls of monolignols are proposed to be important for generating oxidative radicals, cross-linking lignin units, and for storage of lignin precursors (through 4-O-glucosylation). Therefore, chemical modification, for instance methylation, of the para-hydroxyl (i.e., 4-OH) of monolignol is expected to interfere with the synthesis of the lignin polymer. To test this hypothesis, we employed a structure-based protein engineering approach, to investigate the molecular mechanisms of regiospecific O-methylation of lignin precursors and natural phenylpropenes, thereby, creating a set of novel monolignol 4-O-methyltransferases that will produce the non-natural para-methylated monolignols in plants. By expressing these engineered enzymes, we demonstrate the consequences of perturbing the natural lignin precursor pool, particularly in reducing the cross-linking and polymerization of lignin, thus lowering lignin content; meanwhile redirecting metabolic flux into the novel soluble- and the "wall-bound"-phenolic esters that are beneficial to plant health and the cell wall digestibility.

Specifically, we explored the structure-function relationships of two types of functionally distinct but structurally related enzymes, i.e., phenylpropene 4-O-methyltransferase and lignin 3/5-O-methyltransferase, to understand their distinctive regiospecific methylation and substrate discrimination. The resulting information was used to create comprehensive libraries of the variants of lignin 3/5-O-methyltransferase and phenylpropene 4-O-methyltransferase, employing both the approaches of structure-based rational design and the iterative site-directed saturation mutagenesis. With high-throughput colorimetric and/or isotopic functional screening, we selected a range of novel variants able to efficiently methylate the para-hydroxyl of monolignols. The best performing novel engineered monolignol 4-O-methyltransferases were expressed in plants to evaluate their effects on lignin content and composition.

The cell wall of plants represents the most abundant biomass on earth, and is the most promising source of renewable energy. After cellulose, lignin is the second major cell-wall biopolymer of vascular plants; it imparts mechanical strength to the stem and protects the cellulose fiber from chemical- and biological-degradation. Although lignin confers integrity and resistance to the cell wall, its presence there lowers the efficiency of using the cell wall's cellulosic biomass for energy production.

Lignin, a complex biopolymer of hydroxylated and methylated phenylpropane units, is mainly derived from the oxidative coupling of three different hydroxycinnamyl alcohols (or monolignols), i.e., p-coumaryl, coniferyl, and sinapyl alcohols, which differ from each other only by their degree of methoxylation (FIG. 1A). These three monolignols, incorporated into the lignin polymer, produce, respectively, p-hydroxyphenyl (H), guaiacyl (G), and syringyl (S) phenylpropanoid units. The G unit is singly methylated on the 3-hydroxyl group, whereas the S unit is methylated on both the 3- and 5-hydroxyl moieties. The ratio of S-to-G subunits dictates the degree of lignin condensation by allowing different types of polymeric linkages. Increased G content leads to highly condensed lignin composed of a greater portion of biphenyl and other carbon-carbon linkages, whereas S subunits are commonly linked through more labile ether bonds at the 4-hydroxyl position. In angiosperms, lignin is composed of guaiacyl and syringyl monomers, whereas gymnosperm lignin consists almost entirely of guaiacyl moieties. Either or both the reduction of lignin content and increasing the proportion of the more chemically labile S lignin are desirable as such changes would facilitate the degradation of the cell wall.

The biosynthesis of the lignin precursors proceeds through the common phenylpropanoid pathway, starting with the deamination of phenylalanine to cinnamic acid. Subsequent enzymatic reactions include the hydroxylation of the aromatic ring, the activation of cinnamic acids to cinnamoyl-CoA esters, the methylation of certain phenolic hydroxyl groups, and the reduction of the CoA esters to cinnamaldehydes and further to cinnamyl alcohol. The characterization of p-hydroxycinnamoyltransferase and p-coumarate 3-hydroxylase and the demonstration of hydroxylation and methylation reactions occurring preferentially at the cinnamaldehyde and cinnamyl alcohol level led to the significant revision and simplification of the proposed monolignol biosynthetic pathway.

Despite increasing knowledge of the enzymology of monolignol biosynthesis, the processes of plant lignification still are unclear, and the molecular mechanism of lignin polymerization remains controversial.

Monolignol 4-O-Glucosylation and Transport.

Monolignols are formed in the cytosol, after which they are sequestered into cell wall where subsequently they are polymerized to afford a wall-reinforcing biopolymer. The monolignol 4-O-β-D-glucopyranosides, i.e., E-coniferin and E-syringin, frequently accumulate in the cambial region of gymnosperms and some angiosperms. Long-standing hypothesis suggest that these monolignol glucosides may be storage reserves or transport forms of the monolignols, and that the uridine diphosphate glucose (UDPG)-coniferyl/sinapyl alcohol glucosyltransferases, together with coniferin-β-glucosidase may regulate the storage and mobilization of monolignols for lignan/lignin biosynthesis. A few UDPG-glycosyltransferases (UGTs) that 4-O-glucosylate coniferyl alcohol or sinapyl alcohol have been identified in *Arabidopsis*. Reverse genetic studies demonstrated the effects of disturbances in the formation of glycosidic monolignols. However, because UGTs comprise a large superfamily of enzymes that exhibit broad substrate specificity in vitro, it is difficult to precisely demonstrate their specific roles in monolignol 4-O-glycosylation and the roles of such glycosylation in the proposed lignin precursor transport, particularly when this assessment relies only on the reverse genetic approach.

Dehydrogenation of Monolignols and Phenoxy Radical-Radical Coupling.

After monolignols are transported to the cell wall, lignin is formed through oxidative dehydrogenation and subsequent coupling of the resulting phenoxy radicals. The dehydrogenation (single-electron oxidation) of monolignols is believed to be initiated at the para-hydroxyl (4-OH) site of the aromatic ring of the monolignol by oxidative enzymes (peroxidases/laccases), followed by electron delocalization (radical transfer), generating p-quinoid species, i.e., the free radical intermediates (as depicted with p-coniferyl alcohol in FIG. 1B).

The evidence that supports the involvement of the oxidases (peroxidases/laccases) in monolignol dehydrogenation is extensive but circumstantial. Genes for the peroxidases and laccases were cloned from various plant species and their expression and lignification response was examined. A few studies reported reduced lignin content as consequence of reduction in specific peroxidase and laccase expression.

The monolignol radicals generated by dehydrogenation are relatively stable owing to electron resonance, and are subsequently coupled to each other or to the growing polymers during lignification to form the lignin macromolecule. Much controversy has centered on the question of whether phenoxy radical cross-coupling is tightly controlled under protein/template guidance, or is a random chemical process. The cross-coupling of monolignols in lignin polymerization generates different inter-unit bonding, including the most frequent β-O-4 (β-aryl ether) linkage, and less frequent 5-O-4 ether linkage (FIG. 1B); formation of these ether linkages between phenylpropane units directly involves the un-substituted 4-hydroxyl positions.

Reverse Genetic Studies on Lignin Biosynthesis.

Transgenic approaches have been intensively employed to explore the in vivo functions of lignin biosynthetic genes and enzymes. They have produced a growing knowledge of monolignol biosynthesis and also appear to have great biotechnological potential for manipulating plant lignification. Almost all genes encoding the enzymes in monolignol biosynthetic pathways have been down-regulated in different plant species. In many cases, the gene down-regulation reduced lignin content or changed its composition. Interestingly, in a few cases, repressing lignin biosynthesis did not sevefely affect the overall viability; instead, it promoted carbohydrate accumulation and enhanced the enzymatic hydrolysis of the remaining components of the cell wall, thus raising biofuel yield and decreasing processing costs.

Nevertheless, despite such successes in elucidating and manipulating lignin biosynthesis, the reverse genetic approach is not always straightforward. The complexity of monolignol biosynthetic pathways, the metabolic plasticity and the functional redundancy of the families of genes involved (e.g., there are more than 70 peroxidase genes in the *Arabidopsis* genome sequence) added uncertainties and complications to reverse genetic approaches aimed at exploring gene functions, elucidating lignification mechanisms, and biotechnological manipulation of lignin biosynthesis. Thus, additional approaches are desirable to dissect and manipulate plant lignification.

Regiospecific O-Methylation of Lignin Monomeric Precursors and Phenylpropenes.

S-adenosyl-L-methionine (SAM)-dependent methyltransferases are involved in the biosynthesis of a variety of small molecule compounds in plants, such as phenylpropenes, lignin monomeric precursors, flavonoids, isoflavonoids, alkaloids, and polyalcohols. Methylation essentially determines the specific physiological functions of the resultant molecules. In monolignol biosynthesis, the O-methylation of lignin monomeric precursors is catalyzed by two distinct types of O-methyltransferases, namely, caffeate/5-hydroxyferulate 3/5-O-methyltransferase (COMT) and caffeoyl CoA 3-O-methyltransferase (CCoAOMT). COMT, a homodimer with a large subunit of 38-40 KDa, belongs to the plant type I methyltransferase family and does not require metal ions for catalysis. The enzymes from many plant species have been extensively characterized. It was originally recognized as being responsible for methylating caffeic acid and 5-hydroxyferulic acid, and lately was re-evaluated as predominating p-cinnamaldehyde and cinnamyl alcohol methylation. The enzyme displays very broad substrate-specificity in vitro, methylating a range of phenolics with propanoid tails bearing different functionalities (i.e., carboxylate, aldehyde and alcohol); but, for all substrates, it exhibited exclusive regiospecificity for meta (3 or 5)-hydroxylmethylation. The crystal structure of alfalfa COMT has been determined. Ternary complexes with the methyl donor SAM/SAH and substrate caffeic acid/5-hydroxyconiferaldehyde clearly revealed the structural basis for its substrate promiscuity and 3/5-OH specific methylation.

As consequence of the activities of lignin O-methyltransferases, monolignols and their monomeric precursors are methylated only at the meta-positions (i.e., 3-OH or 5-OH) of the phenyl rings (FIG. 1A). The para-hydroxyl position of lignin precursors is never methylated, pointing to the importance of the free para-hydroxyl of monolignol in lignin biosynthesis and polymerization. In fact, in all current lignin biosynthetic scenarios, the free para-hydroxyl of monolignol is implicated to be critical for monolignol dehydrogenation (FIG. 1B), for cross-coupling to form inter-unit linkages, and for glycosylation of monolignols for their storage, and perhaps transport (FIG. 1A). Consistently, our data showed that the phenolic compound bearing the methoxyl moiety at its para-position is inactive in coupling reaction to Gibbs' reagent and in forming in vitro synthetic lignin. Therefore, methylation of the para-hydroxyls (i.e., 4-OH) of monolignols should diminish their polymerization to form lignin.

Several O-methyltransferases characterized from a few plant species are able to catalyze the 4-O-methylation of a group of volatile compounds, the phenylpropenes isoeugenol, eugenol and chavicol. These allylphenols are structural analogs of monolignols, differing only in their propanoid tails. Particularly, isoeugenols closely resemble p-coniferyl alcohol. The characterized phenylpropene 4-OMTs include (iso)eugenol 4-O-methyltransferase (IEMT) from *Clarkia breweri*, eugenol and chavicol 4-O-methyltransferases (EOMT and CVOMT) from sweet basil, and two additional enzymes (SbOMT1 and SbOMT3) from sorghum (Baerson et al, unpublished data). Among them, IEMT from *C. breweri* shares more than 83% sequence identity at the amino acid level with caffeic acid 3-O-methyltransferase (COMT) from the same species, but exhibits distinct substrate preferences and regio-specificity for 4-hydroxyl methylation of phenylpropenes.

Based on sequence analysis, Pichersky and his colleague (Wang and Pichersky, Arch. Biochem. Biophys. 368:172-180 (1999) and Wang and Pichersky, Arch Biochem. Biophys. 349:153-160 (1998)) previously conducted rational mutagenesis on IEMT and COMT and demonstrated that reciprocally replacing strategic amino acid residues of IEMT and COMT could inversely switch both the substrate preference and regiospecificity of two enzymes to each other; i.e., substitution mutations converted IEMT from the 4-O-methylation of isoeugenol to the 3/5-O-methylation of caffeic acid, and switched COMT from the 3/5-O-methylation of caffeic acid to the 4-O-methylation of isoeugenol. These pioneering studies demonstrate the plasticity of these two closely related enzymes. However, their studies did not report any mutant enzymes with 4-O-methylation activity toward lignin monomeric precursors.

Directed Protein Evolution.

Numerous biochemical analyses suggested that the plasticity of proteins, yielding novel or altered functions, rests upon a few amino-acid substitutions. Recently, directed protein evolution has been broadly applied to engineer enzymes with novel functions or improved properties. Among the many sophisticated mutagenesis methods being developed, Gene Site Saturation Mutagenesis (GSSM) represents a very non-stochastic random mutagenesis approach. This comprehensive technique introduces minimally all possible single amino-acid substitutions (up to 19) into the targeted site via degenerate primers. Subsequently combining the single beneficial substitutions into one variant by combinatorial gene reassembly heightens the efficiency of this strategy. In addition to the site mutagenesis, another efficient way to evolve protein's function and property is through DNA family shuffling to create gene chimeras. Since the related enzymes are from the same family and share common folds, the chimeric polypeptides are likely to be functional because they can fold appropriately. One highly efficient DNA family chimeragenic method being developed is "Random Chimeragenesis on Transient Templates" (RACHITT) wherein one single-strand parental DNA is used as a transient template to guide the hybridization of the gene fragments from the homologous gene in the same family to create "mosaic" chimeras. Compared to other conventional in vitro recombination methods like "sexual PCR" gene shuffling and the "staggered extension process", RACHITT generates high resolution recombinatory crossovers at high frequency in gene-family-shuffled libraries (averaging 14 crossovers per gene vs four or fewer using other DNA shuffling methods). Thus, it greatly expands the diversity of chimeric variants. The method has been used both for improving the enzyme catalytic efficiency and substrate specificity.

EXEMPLIFICATIONS

Figure 1A:
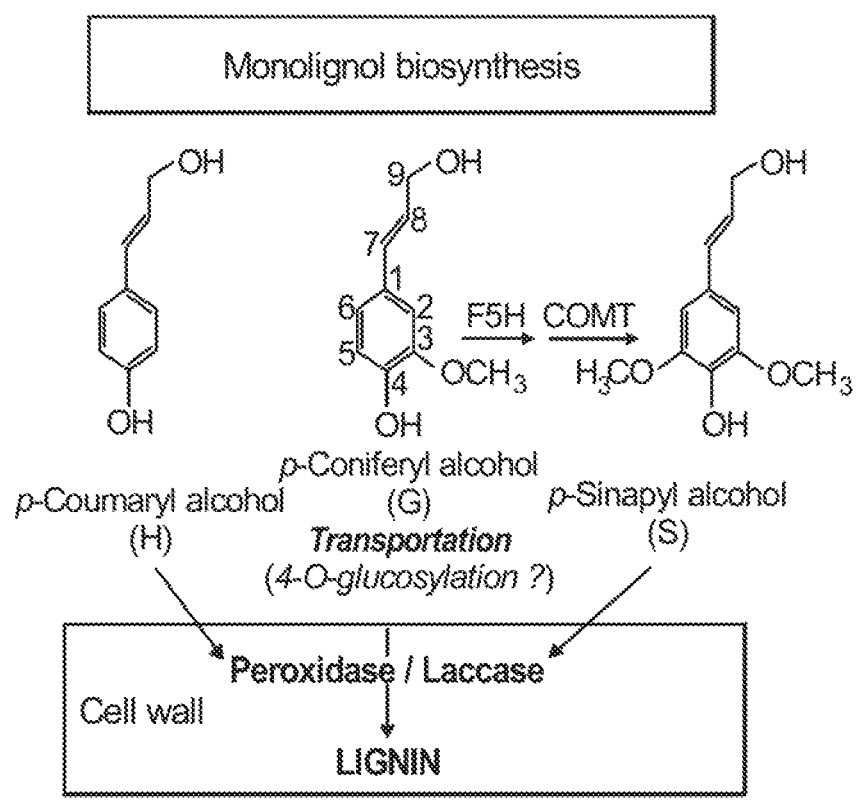
FIG. 1: (A). Scheme of lignin biosynthesis. F5H: ferulate 5-hydroxylase, COMT: caffeic acid 3-O-methyltransferase. Only the catalytic reactions of F5H and COMT at cinnamyl alcohol level are shown, respectively. (B). Oxidase-catalyzed monolignol dehydrogenation, the electron delocalization of radicals and examples of lignin structural units in polymer.
Figure 1B:
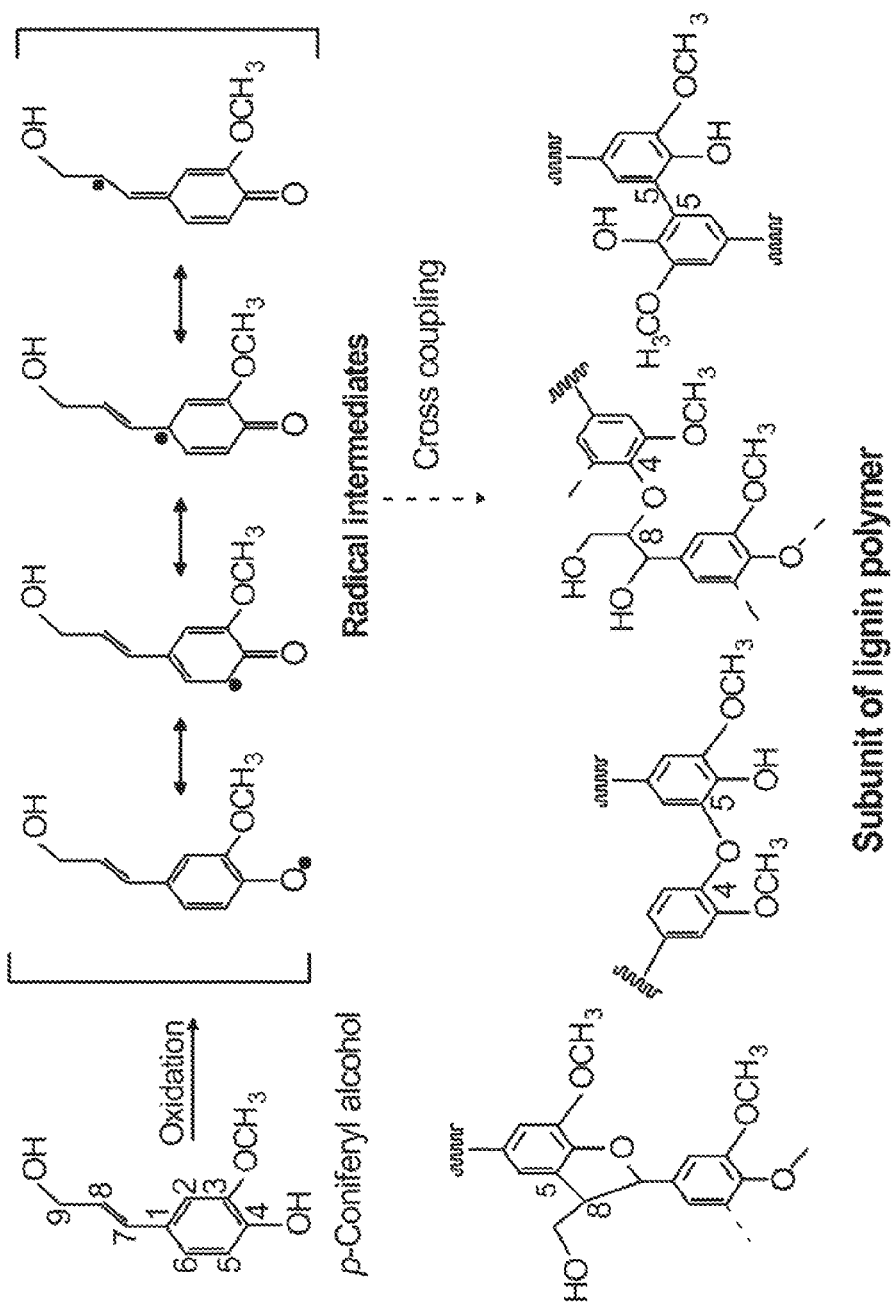

Site Directed Mutagenesis cDNA encoding *C. breweri* IEMT was polymerase chain reaction (PCR) amplified from pET11-IEMT plasmid (Wang, J., et al. (1998) Arch. Biochem. Biophes. 349:153-160) and subcloned into a modified pET28a(+) vector compatible with Gateway® cloning to fuse the IEMT with a His tag to facilitate Ni+-mediated affinity protein purification (Bhuiya, M. W. and Liu, C. J. (2009) Anal. Biochem. 384:151-158).

Saturation mutagenesis was performed at sites 130, 131, 133, 134, 139, 164, 165, 175, 186, 319, 326 and 327 of IEMT (GenBank U86760.1) (SEQ ID NO: 1) following the QuikChange® site-directed mutagenesis strategy (Stratagene) using NNK degenerate primers (N represents a mixture of A, T, G, C, and K for G/T) (see Bhuiya, M. W. and Liu, C. J. (2010) J. Biol. Chem. 285:277-285 and its supplemental material). The codon NNK has 32-fold degeneracy and encodes all 20 amino acids without rare codons.

Mutant Library Screening and Enzymatic Assay

*E. coli* transformants were inoculated in 96 well plates. Protein production was induced with 0.2 mM isopropyl β-D-1-thiogalactopyranoside, and the harvested cell cultures were lysed with 60 µl of BugBuster solution per well (Novagen). Enzymatic activity was screened using the lysates directly or after purification of the recombinant protein in a 96 well purification plate.

Screening was performed in a polypropylene microplate (Bio-Rad) containing 50 µl of the reaction in each well, 500 µM p-coniferyl-alcohol substrates, and 500 µM S-adenosyl-L-methionine augmented with (isotopic assay) or without (LC-MS assay) 0.005 µCi of [methyl-$^{14}$C]S-adenosyl-L-methionine, and 20 µl of lysates or purified protein (Ni$^+$ column eluate). (see Bhuiya, M. W. and Liu, C. J. (2010) J. Biol. Chem. 285:277-285 and its supplemental material).

Characterization of Mutants

Changing IEMT Phe-130 to Thr, Asp, and Cys, or Thr-133 to Ser and/or combining those mutations into the double and triple mutants did not alter the regio selectivity of caffeate/5-hydroxyferulate 3/5-O-methyltransferase (COMT) activity.

To identify the residues that specifically entail the substrate preference of IEMT for monolignols, we examined mutation of seven distinct active site residues as well as several adjacent ones (e.g., Leu-131, Leu-139, Phe-175, Asn-164, and Asn-327). About 30 active IEMT mutant clones were selected from the single site saturation mutant libraries, based on their similar, or higher, methylation activity for coniferyl alcohol than that of the wild-type enzyme. The active clones represented 18 distinct codon mutations. All mutations conferring better methylation activity for coniferyl alcohol occurred at two amino acid sites: Glu-165, the residue that potentially interacts with the phenyl ring of the bound substrate, and, Thr-133, the residue involved in binding the propanoid tail of the compound.

Improving the Catalytic Activity of Mutant Variants

To improve the activity of the single mutant variants for 4-O-methylation of monolignols, we employed iterative saturation mutagenesis on Glu-165 and Thr-133 variants. We used the E165F mutant as the parental enzyme to introduce saturation mutations in all six remaining distinct residues. Additionally we employed T133L and T133M variants to mutate specifically Glu-165 with the 32-fold degenerate primers. A range of double mutants was obtained. Serendipitously, only those variants arising from the combination mutations of Glu-165 and Thr-133 exhibited activity for 4-O-methylation of monolignols. Among them, mutants of T133L/E165F, T133L/E165I, T133M/E165F and T133M/E165I demonstrated 1.5-12.6-fold better activity for coniferyl alcohol compared with their respective single site mutant parents.

By modeling the double mutant variant and docking monolignol into its active site, we identified a range of additional amino acid sites potentially directly contacting, or proximal to the docked monolignol. They included Leu-139 and Phe-175 that might contribute to constructing a hydrophobic cavity to interact with the 3-methoxy group of the bound compound, as do the corresponding residues in COMT. Therefore, to optimize enzymatic activity, we imposed further saturation mutations on those recognized sites via T133L/E165F and T133L/E165I as parental templates. Screening the triple mutant libraries, we identified two mutants, T133L/E165I/F175I (more recently termed MOMT3, i.e., monolignol 4-O methyltransferase-3) and T133L/L139Q/E165F, that exhibited a major increase in their activity on monolignols. Kinetic analysis revealed that the former displays the catalytic efficiency of 1245 and 1463 $M^{-1}$ $s^{-1}$, respectively, for coniferyl and sinapyl alcohols, namely, more than 70-fold increases compared with the wild-type enzyme.

Substitutions in T133L/E165I/F175I, particularly the replacement of Phe-175 with Ile, greatly enlarge the original hydrophobic cavity that apparently contributes to constraining the 3-methoxy group of the bound phenolics in the IEMT and its single or double mutant models. This architectural change entails an artificial hydrophobic binding pocket that can accommodate snugly the meta-methoxy moiety of the compound. Consequently, the docked monolignol in the putative active site of this triple mutant variant displays re-orientation compared with the compound in the wild type, single or double mutants. Such repositioning of the substrate probably facilitates the efficient transmethylation of the 4-hydroxyl moiety.

Because substituting Leu-139 with Gln in the T133L/E165F variant increased enzyme activity on monolignols, we incorporated the mutation of L139Q into the triple mutant T133L/E165I/F175I. However, the resulting quadruple mutant variant kinetically did not show any improvement in binding affinity or catalytic efficiency.

Substrate Specificity of Mutant Variants

The mutant variants, represented by T133L/E165I/F175I and T133L/L139Q/E165F, exhibited high activities for a range of lignin monomeric precursors, the p-hydroxycinnamyl alcohols and p-hydroxycinnamaldehydes. The activity of the wild-type IEMT, by contrast, was barely measurable for all such substrates. Kinetically, the mutant T133L/E165I/F175I equally preferred two major types of monolignols in angiosperms, i.e., coniferyl and sinapyl alcohols, whereas the T133L/L139Q/E165F variant favored coniferyl slightly over the sinapyl alcohol.

Additional Mutagenesis

To further optimize the catalytic efficiency of MOMT on the desired para-methylation of monolignols, based on the crystal structure of MOMT3, we identified additional amino acid residues that either directly contact or are proximate to the bound coniferyl alcohol, particularly the residues near the 3-methoxy-buried pocket. They are F130, A134, V138, L139, F157, Y161, N164, F166, Y168, H169, H173, F179, M183, N186, T319, L322, M323, A325, Y326, and N327. We then carried out the next round saturation mutagenesis on the recognized amino acid sites using MOMT3 as the parental template. Functional screening more than 4500 mutant clones, identified seven tetra- or penta-mutants that showed even higher catalytic activity than MOMT3, with the substitutions at Y161, F166, H169 and A325. Kinetic analyses (Table 1) revealed that the mutants T133L-E165I-F175'-F166W and T133L-E165I-F175I-F166W-H169 (MOMT5) to both coniferyl alcohol and sinapyl alcohol reached up to 4000 ($W^{-1}$ $s^{-1}$), about ~200-fold increase compared with those of the IEMT wild-type enzyme. Their catalytic properties are y is comparable to those of the native phenolic O-methyltransferases. The MOMT4 enzyme predominantly reacted with coniferyl and sinapyl alcohols, with preference for the latter, while the MOMT5 favors for coniferyl alcohol. Mutations in the tetra- and penta-variants largely enhanced the hydrophobicity of the active site and optimized the geometry of the binding pocket for the better holding monolignol substrates.

TABLE 1

Kinetic parameters for 4-O-methylation of coniferyl alcohol and sinapyl alcohol

| | Coniferyl alcohol | | | Sinapyl alcohol | | |
|---|---|---|---|---|---|---|
| IEMT mutant | $K_m$ (μM) | $V_{max}$ (nmol · $mg^{-1}$ · $min^{-1}$) | $K_{cat}/K_m$ ($M^{-1}$ · $S^{-1}$) | $K_m$ (μM) | $V_{max}$ (nmol · $mg^{-1}$ · $min^{-1}$) | $K_{cat}/K_m$ ($M^{-1}$ · $S^{-1}$) |
| IEMT wt | 1591 ± 182 | 42 ± 4 | 18 | 1495 ± 214 | 45 ± 4 | 20 |
| T13M-E165F | 546 ± 62 | 353 ± 19 | 431 | 326 ± 59 | 85 ± 6 | 174 |
| T133L-E165F | 280 ± 18 | 117 ± 3 | 279 | 382 ± 32 | 103 ± 4 | 180 |
| T133I-E165I-F175I | 279 ± 48 | 556 ± 35 | 1328 | 120 ± 15 | 275 ± 10 | 1528 |
| | 199 ± 24 | 371 ± 15 | 1246 | 119 ± 11 | 260 ± 6 | 1463 |
| T133I-E165I-F175I-Y161W | 196 ± 34 | 584 ± 37 | 1986 | 219 ± 19 | 259 ± 8 | 788 |
| T133I-E165I-F175I-Y161F | 197 ± 21 | 642 ± 24 | 2172 | 206 ± 25 | 289 ± 12 | 935 |
| T133I-E165I-F175I-F166W | 117 ± 15 | 496 ± 8 | 2825 | 47 ± 8 | 147 ± 4 | 2085 |
| T133I-E165I-F175I-H169F | 193 ± 25 | 793 ± 32 | 2739 | 68 ± 11 | 408 ± 17 | 3999 |
| T133I-E165I-F175I-H169M | 220 ± 27 | 629 ± 26 | 1905 | 89 ± 10 | 370 ± 11 | 2771 |
| T133I-E165I-F175I-A325V | 236 ± 50 | 446 ± 33 | 1260 | 97 ± 7 | 214 ± 4 | 1471 |
| T133I-E165I-F175I-Y326F-N327V | 196 ± 44 | 520 ± 25 | 1768 | 340 ± 30 | 429 ± 15 | 841 |

TABLE 1-continued

Kinetic parameters for 4-O-methylation of coniferyl alcohol and sinapyl alcohol

| IEMT mutant | Coniferyl alcohol | | | Sinapyl alcohol | | |
|---|---|---|---|---|---|---|
| | $K_m$ (µM) | $V_{max}$ (nmol·mg$^{-1}$·min$^{-1}$) | $K_{cat}/K_m$ (M$^{-1}$·S$^{-1}$) | $K_m$ (µM) | $V_{max}$ (nmol·mg$^{-1}$·min$^{-1}$) | $K_{cat}/K_m$ (M$^{-1}$·S$^{-1}$) |
| T133I-E165I-F175I-F166W-H169F | 80 ± 6 | 440 ± 10 | 3666 | 37 ± 7 | 124 ± 7 | 2234 |
| T133I-E165I-F175I-F166W-H169W | 127 ± 8 | 392 ± 9 | 2057 | 67 ± 10 | 160 ± 12 | 1591 |
| T133I-E165I-F175I-F166W-T135N | 167 ± 11 | 431 ± 12 | 1720 | 54 ± 14 | 115 ± 9 | 1420 |

Effects on Dehydrogenative Polymerization In Vitro

In vitro dehydrogenative polymerization is commonly used as a biomimetic model to explore in vivo lignin formation. Using the novel mutant variants, we produced methylated monolignol—the 4-O-methoxy-coniferyl alcohol, and subjected it to peroxidase-catalyzed dehydrogenative polymerization, compared to the classic p-coniferyl alcohol. After incubating these phenolics with horseradish peroxidase and $H_2O_2$, coniferyl alcohol was oxidized and conjugated, yielding several oligolignols, as expected. The oligomer products include a predominant dimer, the β-5 inter subunit linkage, G(8-5)G, and a few minor peaks of the G(8-O-4)G and G(8-8)G dimers. However, essentially no conversion and no oligomerization was observed when 4-O-methylated coniferyl alcohol was incubated with the peroxidase and peroxide.

Incorporation of IEMT Variants in Plants

To further explore whether the 4-O-methylation of monolignols perturbs the oxidative radical generation and the coupling in situ for lignin polymerization, we expressed a MOMT4 tetra mutant (T133L-E165I-F175I-H169F) in *Arabidopsis*, together with the wild type IEMT and a loss-of-function mutant variant (E165R) as the controls. All genes were driven by a PAL2 promoter, which controls the expression of phenylalanine ammonium lyase, the first key enzyme in phenylpropanoid-lignin biosynthetic pathway. The expression of transgenes in both T1 and T2 generations were examined by RT-PCR and qRT-PCR.

Lignin and the related phenolics under UV light produce a typical blue autofluorescence. When cross sections of the first internode of the stem were examined under epi-fluorescence microscopy, the intensity of autofluorescence, and the layers of fluorescent cells within the interfascicular fibers and vascular bundle of xylem of the transgenic lines were obviously weaker and less than those of the control stem. When cross-sections were stained with phloroglucinol-HCl reagent, which produces a violet-red color reaction with hydroxycinnamaldehyde end groups in lignin and thus is used conventionally for monitoring the total lignin, the MOMT4 overexpression plants showed a weaker staining in their vasculatures. In addition, the Mäule staining that differentiates S lignin subunits (red) from G subunits (brown) revealed that sections of MOMT overexpression plants also showed less intense red coloration than the control plants, in particularly, in the fibers of vasculature, indicative of the reduced deposition of lignin monomers. These histochemical data suggest that total lignin content in MOMT4 overexpression lines is reduced.

To determine quantitative alteration of lignin deposition as the consequence of the expression of MOMT4, the T2 generation of four independent transgenic lines were grown with the control plants side by side and used for analyzing lignin content and compositions. The total lignin content was quantified using acetyl bromide method. Decreased levels of total lignin were observed in all transgenic plants, compared to the controls. The maximum lignin reduction was up to 24% in the cell walls of the line MOMT4-3 (Table 2).

TABLE 2

| Genotype | Total Acetyl Bromide Lignin (mg/g CWR) |
|---|---|
| Control | 148.49 ± 3.77 |
| MOMT4-1 | 128.81 ± 3.25 |
| MOMT4-2 | 130.63 ± 2.32 |
| MOMT4-3 | 113.47 ± 1.90 |
| MOMT4-4 | 126.62 ± 2.2 |

Novel Wall Bound Phenolics

The secondary cell walls of monocot grasses and some dicot species including *Arabidopsis thaliana* contain significant quantities of hydroxycinnamates, primarily ferulic acid and p-coumaric acid. These hydroxycinnamates, the so-called "wall-bound" phenolics, mostly link to the C5 carbon of the arabinosyl side chain of arabinoxylans through an ester bond. The bound ferulate residues can dimerize or polymerize with each other, or with other cell-wall polyphenolics presumably via oxidative coupling as does lignin polymerization to form ester-to-ether linkages that cross-link the adjacent polysaccharides, lignins, and/or structural proteins. It is also suggested that polysaccharide-bound ferulate esters may act as nucleation sites for the lignin polymers that anchor lignins to polysaccharides via ether bonds.

The wall-bound phenolics of the MOMT transgenic plants were examined after mild alkaline treatment of cell wall materials. In addition to p-coumarate and ferulate, additional phenolics were incorporated specifically in the walls of MOMT transgenic plants. The UV and Mass spectra and the fragmentation behaviors in the tandem MS analysis identified them as 4-O-methoxyferulic acid and 4-O-methoxysinapic acid. Quantifying the amount of the incorporated phenolics in both the transgenic and control plants revealed that the overexpression line, MOMT4-3, with maximum lignin reduction showed the highest accumulation level of both 4-O-methoxyferulic acid and 4-O-methoxysinapic acid, indicating the redirection of the non-nature monolignols. This phenomenon would involve an acyltransferase activity catalyzing the transfer of the activated 4-O-methoxyferuloyl/sinapoyl from the donor molecule (presumably CoA-thioester or 1-O-glucoside) to the polysaccharides. The "wall-bound" phenolic moieties and their cross links have profound implication on cell wall structure property. They greatly affect the cell wall feedstock digestibility. Incorporating novel 4-O-methylated ester-bound compounds might diminish the formation of ester to ether linkage or the dimerization, thus being a potential strategy to mitigate the cross-linkage of lignin and polysaccharides, therefore, improve the digestibility.

In addition to lignin and "wall-bound" phenolics, we examined the polysaccharide cellulose content in the cell wall of transgenic plants. Although varied in extent, there is no significant difference of cellulose deposition between control and the most MOMT overexpression plants.

We then performed the saccharification assay to evaluate the acceptability of cell walls for bioconversion to products. The samples were exposed to cellulases and other enzymes that specifically hydrolyze cell wall carbohydrates. Compared with control plants, transgenic lines showed significant increases in releasing the neutral sugar from cellulose fibers of the cell walls of MOMT overexpression plants, without mild acid pretreatment. The MOMT transgenic lines showed up to 22% increase in releasing sugars from cell walls.

Accumulation of Novel UV Resistant Phenolic Compounds

Arabidopsis thaliana and other members of the Brassicaceae accumulate sinapate esters, predominantly sinapoylmalate in leaves and sinapoylcholine in seeds (Chapple et al. The Plant cell 4, 1413-1424 (1992)). Sinapate esters and flavonol glycosides are considered as protectants against UV irradiation. To investigate whether perturbation of monolignol flux to lignin polymerization will affect other phenylpropanoid metabolisms, we profiled the methanol-soluble phenolics from MOMT4 transgenic and control stems, leaves and roots. In addition to sinapoylmalate and flavonols found in the leaf and stem extracts from both the overexpression and control plants, two bona fide phenolic conjugates with the molecule mass of 323 and 353 m/z, respectively, were found exclusively in the extracts of MOMT4 transgenic plants. MSn analysis identified them as the 4-O-methoxyferuloyl malate and 4-O-methoxysinapoyl malate. Correspondingly, the 4-O-methoxyferuloyl glucoside was accumulated in the roots of the MOMT4 overexpression plants. Consistent with PAL2 promoter expressing patterns that was mainly in root, stem and leaf epidermis cells, the 4-O-methoxylsinapate/ferulate esters were not found in the mature seeds. The accumulation levels of the soluble 4-O-methylated compounds were consistent with the variable expression of MOMT4 in transgenic lines. These data suggest that accumulation of 4-O-methoxycinnamate esters results from the activity of the expressed MOMT4.

This study reveals that introducing a non-native enzyme that reduces para-hydroxyl deprotonation propensity perturbs lignin polymerization, which is concomitantly associated with rerouting flux to the novel 4-O-methylated "wallbound" phenolics and the UV protectant methanolic phenolic derivatives. These data emphasize the remarkable plasticity of Arabidopsis phenylpropanoid metabolism.

MOMT4-Mediated Reduction of Lignin does not Compromise the Plant Growth and Development Although high expression of MOMT4 transgene resulted in significant reduction of cell wall lignin content, the transgenic plants did not show a discernible morphological phenotype, compared to the wild-type and control plants. The vasculature of the overexpression line and control plants showed no obvious anatomic differences.

To further examine whether expressing the artificial MOMT and producing novel phenolics would potentially impose feedback regulation on global gene expression, we conducted transcriptomic analysis on MOMT transgenic lines. Among the more than 22000 genes detected, only 12 showed a moderate change in their expression levels and none of them showed a clear function in the central metabolic or regulatory pathways.

These results imply that manipulating lignin biosynthesis at the last step of pathway will lead to minimal deleterious effect on plant growth and development while still producing the desired effect of enhancing the digestibility of the lignin that is formed.

The same strategy is applied to modulating lignin biosynthesis in Populus (hybrid aspen). Target plants may include but are not limited to Arabidopsis, corn, rice, switchgrass, poplar and other angiosperms and gymnosperms.

Successful incorporation and expression of the mutant enzymes will modify the complexity and amounts of lignin in the modified plants, with some expectation that the plants will provide an improved source of biomass for conversion to biofuels.

The invention claimed is:

1. A modified (iso)eugenol 4-O-methyltransferase (IEMT) enzyme having three amino acid substitutions selected from the group consisting of enzymes having amino acid substitutions T133L/E165I/F175I and T133L/L139Q/E165F, wherein the modified amino acid residues correspond to those of SEQ ID NO: 1.

2. An isolated nucleic acid molecule encoding a modified (iso)eugenol 4-O-methyltransferase enzyme having three amino acid substitutions selected from the group consisting of sequences encoding amino acid substitutions T133L/E165I/F175I and T133L/L139Q/E165F, wherein the modified amino acid residues correspond to those of SEQ ID NO: 1.

3. An expression vector adapted for expression in plants of a modified IEMT enzyme comprising the nucleic acid sequence of claim 2.

4. A plant containing the expression vector of claim 3.

5. The plant of claim 4 selected from the group consisting of *Arabidopsis*, poplar, corn, rice and switchgrass.

6. A modified (iso)eugenol 4-O-methyltransferase enzyme having four or five amino acid substitutions selected from the group consisting of enzymes having amino acid substitutions T133L/E165I/F175I/F166W, T133L/E165I/F175I/H169F, T133L/E165I/F175I/F166W/H169W, T133L/E165I/F175I/F166W/H169F, T133I/E165I/F175I/Y326F/N327V and T133L/E165I/F175I/F166W/T135N, wherein the modified amino acid residues correspond to those of SEQ ID NO: 1.

7. An isolated nucleic acid sequence encoding the modified (iso)eugenol 4-O-methyltransferase enzyme of claim 6.

8. An expression vector adapted for expression in plants specifically designed to express the modified IEMT enzyme sequence of claim 7.

9. A plant containing the expression vector of claim 8.

10. The plant of claim 9 selected from the group consisting of *Arabidopsis*, poplar, corn and switchgrass.

11. A modified (iso)eugenol 4-O-methyltransferase (m-IEMT) having an increased activity, compared to wild type (iso)eugenol 4-O-methyltransferase (wt-IEMT), for 4-O-methylation of coniferyl alcohol or sinapyl alcohol or both, said m-IEMT having three, four or five amino acid substitutions selected from the group consisting of T133L/E165I/F175I, T133L/L139Q/E165F, T133L/E165I/F175I/F166W, T133L/E165I/F175H/H169F, T133L/E165I/F175I/F166W/H169W, and T133L/E165I/F175I/F166W/H169F, wherein the modified amino acid residues correspond to those of SEQ ID NO: 1.

* * * * *

SEQUENCE LISTING

<160> NUMBER OF SEQ ID NOS: 1

<210> SEQ ID NO 1
<211> LENGTH: 368
<212> TYPE: PRT
<213> ORGANISM: Clarkia breweri

<400> SEQUENCE: 1

```
Met Gly Ser Thr Gly Asn Ala Glu Ile Gln Ile Ile Pro Thr His Ser
1               5                   10                  15

Ser Asp Glu Glu Ala Asn Leu Phe Ala Met Gln Leu Ala Ser Ala Ala
            20                  25                  30

Val Leu Pro Met Ala Leu Lys Ala Ala Ile Glu Leu Asp Val Leu Glu
        35                  40                  45

Ile Met Ala Lys Ser Val Pro Pro Ser Gly Tyr Ile Ser Pro Ala Glu
    50                  55                  60

Ile Ala Ala Gln Leu Pro Thr Thr Asn Pro Glu Ala Pro Val Met Leu
65                  70                  75                  80

Asp Arg Val Leu Arg Leu Leu Ala Ser Tyr Ser Val Val Thr Tyr Thr
                85                  90                  95

Leu Arg Glu Leu Pro Ser Gly Lys Val Glu Arg Leu Tyr Gly Leu Ala
            100                 105                 110
```

-continued

```
Pro Val Cys Lys Phe Leu Thr Lys Asn Glu Asp Gly Val Ser Leu Ala
        115                 120                 125

Pro Phe Leu Leu Thr Ala Thr Asp Lys Val Leu Leu Glu Pro Trp Phe
        130                 135                 140

Tyr Leu Lys Asp Ala Ile Leu Glu Gly Gly Ile Pro Phe Asn Lys Ala
145                 150                 155                 160

Tyr Gly Met Asn Glu Phe Asp Tyr His Gly Thr Asp His Arg Phe Asn
                165                 170                 175

Lys Val Phe Asn Lys Gly Met Ser Ser Asn Ser Thr Ile Thr Met Lys
                180                 185                 190

Lys Ile Leu Glu Met Tyr Asn Gly Phe Glu Gly Leu Thr Thr Ile Val
        195                 200                 205

Asp Val Gly Gly Gly Thr Gly Ala Val Ala Ser Met Ile Val Ala Lys
        210                 215                 220

Tyr Pro Ser Ile Asn Ala Ile Asn Phe Asp Leu Pro His Val Ile Gln
225                 230                 235                 240

Asp Ala Pro Ala Phe Ser Gly Val Glu His Leu Gly Gly Asp Met Phe
                245                 250                 255

Asp Gly Val Pro Lys Gly Asp Ala Ile Phe Ile Lys Trp Ile Cys His
                260                 265                 270

Asp Trp Ser Asp Glu His Cys Leu Lys Leu Leu Lys Asn Cys Tyr Ala
        275                 280                 285

Ala Leu Pro Asp His Gly Lys Val Ile Val Ala Glu Tyr Ile Leu Pro
        290                 295                 300

Pro Ser Pro Asp Pro Ser Ile Ala Thr Lys Val Val Ile His Thr Asp
305                 310                 315                 320

Ala Leu Met Leu Ala Tyr Asn Pro Gly Gly Lys Glu Arg Thr Glu Lys
                325                 330                 335

Glu Phe Gln Ala Leu Ala Met Ala Ser Gly Phe Arg Gly Phe Lys Val
                340                 345                 350

Ala Ser Cys Ala Phe Asn Thr Tyr Val Met Glu Phe Leu Lys Thr Ala
        355                 360                 365
```